(12) United States Patent
Ebers et al.

(10) Patent No.: US 8,016,478 B2
(45) Date of Patent: Sep. 13, 2011

(54) MULTISTATION DEVICE FOR MIXING THE CONTENTS OF LABORATORY VESSELS

(75) Inventors: Manfred Ebers, Bonningstedt (DE);
Bernd Petersen, Itzstedt (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 12/529,514

(22) PCT Filed: Mar. 3, 2008

(86) PCT No.: PCT/EP2008/001646
§ 371 (c)(1),
(2), (4) Date: Jul. 28, 2010

(87) PCT Pub. No.: WO2008/107139
PCT Pub. Date: Sep. 12, 2008

(65) Prior Publication Data
US 2010/0284238 A1   Nov. 11, 2010

(30) Foreign Application Priority Data
Mar. 2, 2007   (DE) .......................... 10 2007 010 616

(51) Int. Cl.
*B01F 11/00* (2006.01)
(52) U.S. Cl. ....................................................... 366/208
(58) Field of Classification Search .......... 366/108–117, 366/208–219, 124
See application file for complete search history.

(56) References Cited

U.S. PATENT DOCUMENTS

| | | | |
|---|---|---|---|
| 3,310,292 A | 3/1967 | Moore | |
| 3,430,926 A * | 3/1969 | Liobis et al. | 366/212 |
| 4,047,704 A * | 9/1977 | Hawrylenko | 366/198 |
| 5,346,303 A * | 9/1994 | Heinonen et al. | 366/208 |
| 5,372,425 A * | 12/1994 | Tannenbaum et al. | 366/208 |
| 5,593,228 A * | 1/1997 | Tannenbaum | 366/209 |
| 5,988,869 A * | 11/1999 | Davidson et al. | 366/208 |
| 7,338,199 B2 * | 3/2008 | Hafner | 366/208 |
| 2007/0177457 A1 | 8/2007 | Hafner | |
| 2007/0211566 A1 * | 9/2007 | Ebers et al. | 366/208 |
| 2007/0212265 A1 * | 9/2007 | Ebers et al. | 422/99 |
| 2010/0284238 A1 * | 11/2010 | Ebers et al. | 366/110 |

FOREIGN PATENT DOCUMENTS

| | | |
|---|---|---|
| DE | 100-38-060 | 5/2001 |
| DE | 202-18-573 | 4/2003 |
| DE | 20-2006-001514 | 5/2006 |
| EP | 1201297 | 5/2002 |
| EP | 1832335 | 9/2007 |
| EP | 1832336 | 9/2007 |
| JP | 02187138 A * | 7/1990 |
| JP | 07047255 A * | 2/1995 |

* cited by examiner

*Primary Examiner* — Charles E Cooley
(74) *Attorney, Agent, or Firm* — White & Case LLP

(57) ABSTRACT

The invention relates to a multistation mixing device for mixing the contents of laboratory vessels. The device comprises at least two adapter plates having a holder for receiving laboratory vessels and a drive mechanism capable of driving the adapter plates in a mixing motion with the same angular speed such that, in horizontal planes, each point of the adapter plates performs a circular motion with the same radius, the same angle speed and the same angular position around a respective center. The starting positions of the adapter plates, from which the adapter plates are driven by the drive mechanism, are rotated relative to one another by an angle in the direction of the mixing motion in their respective angular position, such that imbalances occurring during the mixing motion are at least partially compensated.

5 Claims, 3 Drawing Sheets

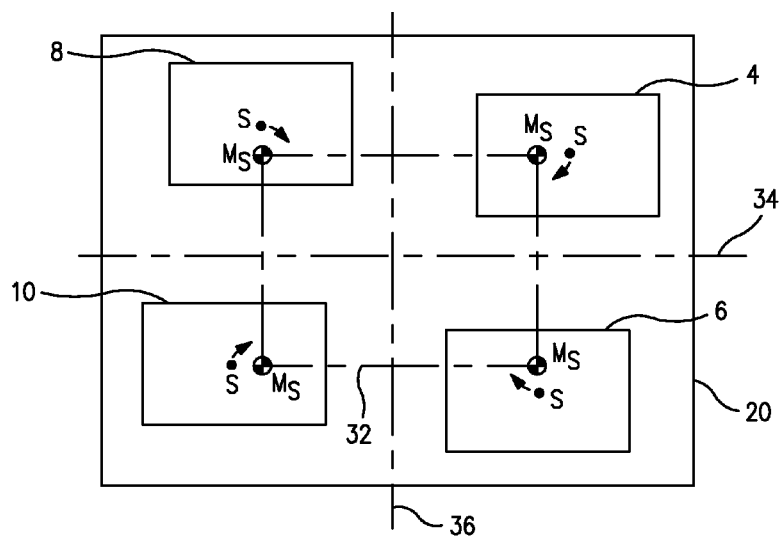
FIG. 2
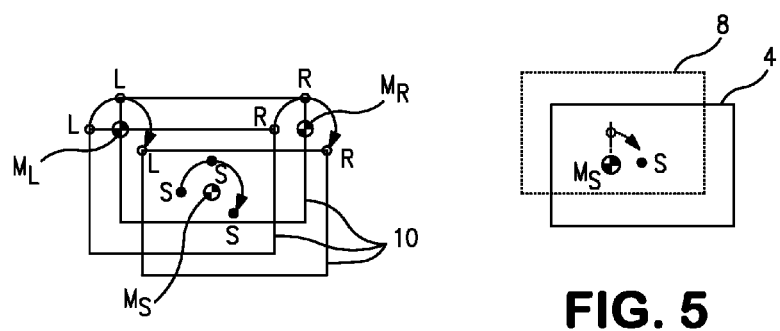
FIG. 4
FIG. 5

MULTISTATION DEVICE FOR MIXING THE CONTENTS OF LABORATORY VESSELS

FIELD OF THE INVENTION

The present invention relates to a device for mixing the contents of laboratory vessels in particular, with at least two adapter plates, each with a holder for receiving vessels, in particular laboratory vessels in exchangeable thermoblocks, and with a drive mechanism, by means of which each of the adapter plates can be driven with the same angular speed in a mixing movement which oscillates in a circular translatory manner in a horizontal plane.

Mixing devices in which the contents of vessels are mixed are sufficiently well known. For laboratories in particular, there are mixers that can also mix small amounts of liquid by virtue of the fact that small containers are also combined in very large groups of tens, hundreds or even thousands in suitable holders, called "exchangeable thermoblocks". Such exchangeable thermoblocks and also the reaction vessels can be standardized. For example, there are reaction vessels with a content of 0.2 ml, 0.5 ml, 1.5 ml and 2.0 ml, and respective suitable exchangeable thermoblocks which are standardized for these. In addition, there are, for example, exchangeable thermoblocks for cryo tubes, for Falcon tubes (1.5 ml and 50 ml), for glass vessels and glass beakers, for microtiter plates (MTP), for deepwell plates (DWP), for slides, and for PCR plates with 96 wells. This list is not exhaustive, but it indicates the wide variety of laboratory vessels which exist and for which the mixers should be suitable. For this purpose, there are standards and rules governing the so-called "footprints", namely the base structure of exchangeable thermoblocks.

Since these exchangeable thermoblocks are in principle designed in such a way that the individual vessels are inserted into them from above, a mixing movement which oscillates in a circular and translatory manner and takes place substantially in a horizontal plane has become established for the known mixers. For this purpose, in the known mixers, an electromotive imbalance drive is generally responsible for driving a "table" in this circular movement. To this end, said table is known to be mounted in different ways. For example, mounting in linear rolling bearings (so-called spherical bushes) in the two horizontal directions is known, although film-hinge bearings are also known. Alternatively, there is also electromagnetic mounting or mounting using piezoelements which can each likewise also be used as a drive.

EP 1201297 A1 discloses a shaker apparatus for sample vessels, in particular also for microtiter plates, which apparatus has at least one dedicated electromagnetic drive mechanism for each sample vessel supporting table.

Such mixers are usually driven at a rotational frequency of 200 rpm to 1500 rpm. It is known that the frequency of the mixing movement can be set on the basis of the mixing required for the mixing material, but also on the basis of mechanical mixing parameters.

It has proven useful, particularly in large-scale laboratory operation, to use what are known as multistation mixers. Thus, for example, U.S. Pat. No. 5,372,425 discloses a multi-platform shaker apparatus for sample vessels. For exchangeable thermoblocks in particular, these are suitable in particular for receiving several exchangeable thermoblocks simultaneously for mixing laboratory vessels and for thus driving a greater number of laboratory vessels simultaneously in a mixing movement. A shaker apparatus with a drive mechanism for a single mixer plate that can receive four supports for vessels is disclosed in U.S. Pat. No. 3,310,292.

By contrast, the shaker apparatus from EP 1201297 A1 has, in one embodiment, several vessel supporting tables, each with its own drive mechanism.

The imbalance problem arises physically from the described circular mixing movement. This problem is solved by a suitably placed counterweight which communicates with the rotationally driven adapter plate and rotates too for compensation of the imbalance. Even in a single-station mixer, a counterweight of this kind represents an additional structural part that has to be adjusted during assembly and that further increases the weight of the device as a whole. In multistation mixers, this problem multiplies, so to speak, with the number of adapter plates of the multistation mixing device.

By contrast, the object of the present invention is to provide a multistation mixing device which is imbalance-compensated and is lighter and more energy-efficient and is composed of fewer parts.

This object is achieved by a mixing device as described herein. Preferred embodiments are also disclosed.

SUMMARY OF THE INVENTION

According to the invention, a mixing device, in particular for mixing the contents of laboratory vessels, is provided with an adapter plate and a drive mechanism. The adapter plate has a holder which is suitable for receiving vessels. This is preferably intended to mean that the vessels can be introduced into the holder of the adapter plate in such a way that they are not released by themselves during undisturbed operation during the mixing movement in which the adapter plate can be driven using the drive mechanism. The holder of the adapter plate preferably meets particular standards, in particular with regard to connection dimensions, in particular for laboratory vessels in exchangeable thermoblocks.

The drive mechanism of the mixing device according to the invention is capable of moving the adapter plate in a mixing movement which oscillates in a circular and translatory manner in a plane. "Oscillates in a circular and translatory manner" can in other words be described by the fact that, in such a mixing movement according to the invention, each point of the adapter plate executes a circular movement with the same radius, the same angular speed and the same angular position about a respective midpoint in parallel planes. The mixing movement takes place in horizontal planes, with the result that exchangeable thermoblocks received in the adapter plates are mixed in an operationally reliable manner with reaction vessels arranged upright in them.

The device according to the invention is characterized by adapter plates whose starting positions, from which they begin the circular translatory oscillating mixing movement with the same angular speed, are rotated relative to one another about their respective rotational midpoints, in particular in such a way that the imbalances generated by their respective circular mixing movement during operation are at least partially compensated.

"Rotated relative to one another" is intended to signify that the starting position of an adapter plate at the start of the circular mixing movement deviates, by the defined angle, from the starting position of another adapter plate about the respective rotational midpoints of the mixing movement.

For this purpose, the drive mechanism of the mixing device drives the adapter plates particularly preferably in the same direction of rotation.

It is also preferable, in a plan view of the device according to the invention, that the adapter plates are arranged mirror-symmetrically and/or uniformly on an imaginary circle. For example, four adapter plates are mirror-symmetrical not only with respect to one line of symmetry, but also to a second one (at right angles to the first line of symmetry). Or, for example, three adapter plates preferably form an equilateral triangle, in which case the adapter plates are then arranged mirror-symmetrically with respect to three lines of symmetry, which lie at 120° to one another, and are arranged uniformly on an imaginary circle. The four adapter plates can be arranged relative to one another at the corners of an imaginary rectangle, that is to say mirror-symmetrically to each other with respect to two lines of symmetry that are at right angles to each other. A square arrangement of the four adapter plates is also possible here, such that the adapter plates (as also in the three adapter plates whose axes of rotation are arranged to form an equilateral triangle) are arranged uniformly on an imaginary circle. A further example that can be mentioned involves six adapter plates, which can form a uniform hexagon.

Arranged for example on the mixing device in the manner described above, the starting positions of the adapter plates (from which they begin the mixing movement with the same angular speed) are rotated relative to one another about their respective rotational midpoints by an angle which is preferably calculated from 360° divided by the total number of adapter plates. For example, four adapter plates are consequently rotated relative to one another through 90°, three adapter plates through 120°, and six adapter plates through 60°. To emphasize it once again, "rotated relative to one another" is intended to signify that the starting position of an adapter plate at the start of the circular mixing movement deviates, by the defined angle, from the starting position of another adapter plate about the respective rotational midpoints.

Moreover, especially when the adapter plates are arranged in the manner described, it is particularly preferable that the starting positions of the diametrically opposite adapter plates are rotated relative to one another through 180°. For example, in the case of six adapter plates which are arranged approximately on a rectangle (four at the corners of the rectangle, and each of the other two at the middle of one of the long sides of the rectangle), the two adapter plate pairs lying diagonally opposite each other on the corners are rotated relative to each other through 180°, likewise the pair of adapter plates lying opposite each other at the middle of the long sides of the rectangle. The starting position from one pair to the other pair then differs once again preferably by 60°.

It will be noted in general that the imbalance compensation achieved according to the invention may not physically function in an ideal way, because the adapter plates may be charged with different loads. It is therefore advantageous, according to the invention, that the imbalances according to the invention at least partially compensate each other and/or are at least reduced in rotation phase.

Further advantages and features of the present invention are described below with reference to the attached drawings which depict an illustrative embodiment of the invention.

BRIEF DESCRIPTION OF THE DRAWINGS

FIG. 2 shows a schematic plan view of the four adapter plates of the device according to FIG. 1, FIG. 4 shows a schematic plan view of one of the four adapter plates according to FIG. 2 in order to illustrate the circular translatory oscillating mixing movement, and FIG. 5 shows a schematic plan view of one of the four adapter plates according to FIG. 2 in order to illustrate the inventive rotation of the starting position in the direction of the mixing movement.

DETAILED DESCRIPTION OF THE INVENTION

Figure 1:
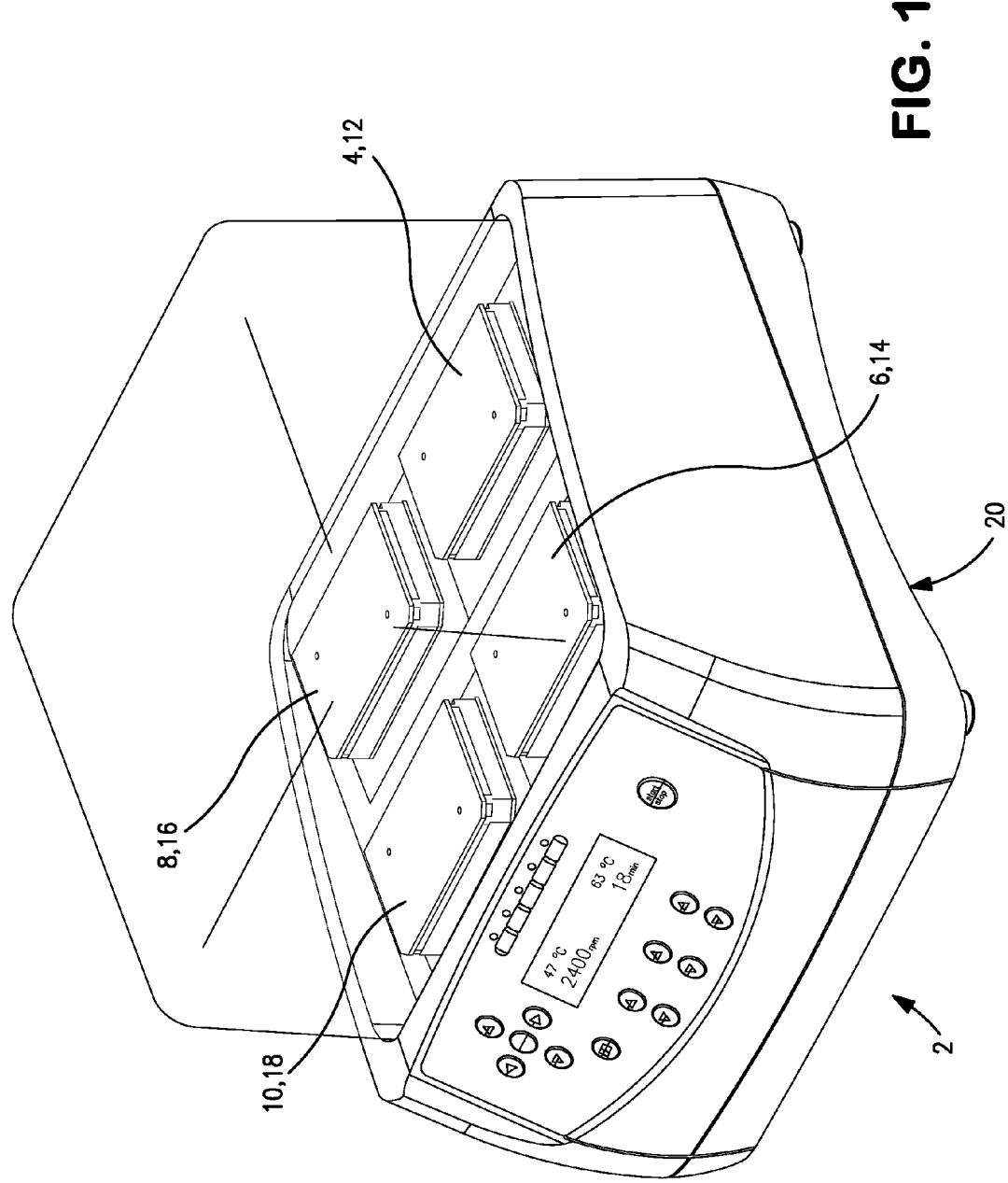
FIG. 1 shows a three-dimensional view of a mixing device according to the invention with four adapter plates.

In FIG. 1, a mixing device 2 can be seen with four frame-shaped adapter plates 4, 6, 8 and 10 which are arranged on the top and which each have a holder for receiving exchangeable thermoblocks 12, 14, 16 and 18. By means of a drive mechanism inside a housing 20 of the mixing device 2, each of the adapter plates can be driven in a mixing movement that takes place with the same angular speed of each adapter plate 4, 6, 8 and 10, such that, in a horizontal plane, each point of a respective adapter plate executes a circular movement with the same radius, the same angular speed and the same angular position about a respective midpoint (circular translatory oscillating mixing movement). The drive mechanism 22, provided for this purpose in the mixing device 2, and the bearings 24, 26, 28 and 30 of the adapter plates 4, 6, 8 and 10 are shown in FIG. 3, and a schematic representation of the circular translatory oscillating mixing movement can be seen in FIG. 4.

Referring first to FIG. 4: In the circular translatory oscillating mixing movement (of each of the adapter plates 4, 6, 8 and 10 of the mixing device 2; adapter plate 10 is shown by way of example), each point, as can be seen in FIG. 4, of the adapter plate (the top left-hand corner L and right-hand corner R and also the center of gravity S of the adapter plate are highlighted by way of example) moves in a horizontal plane (drawing plane in FIG. 4) on a circular path (shown by the three arrows of circular profile) with the same radius, the same angular speed and the same angular position about a respective midpoint $M_L$, $M_R$ and $M_S$.

Figure 3:
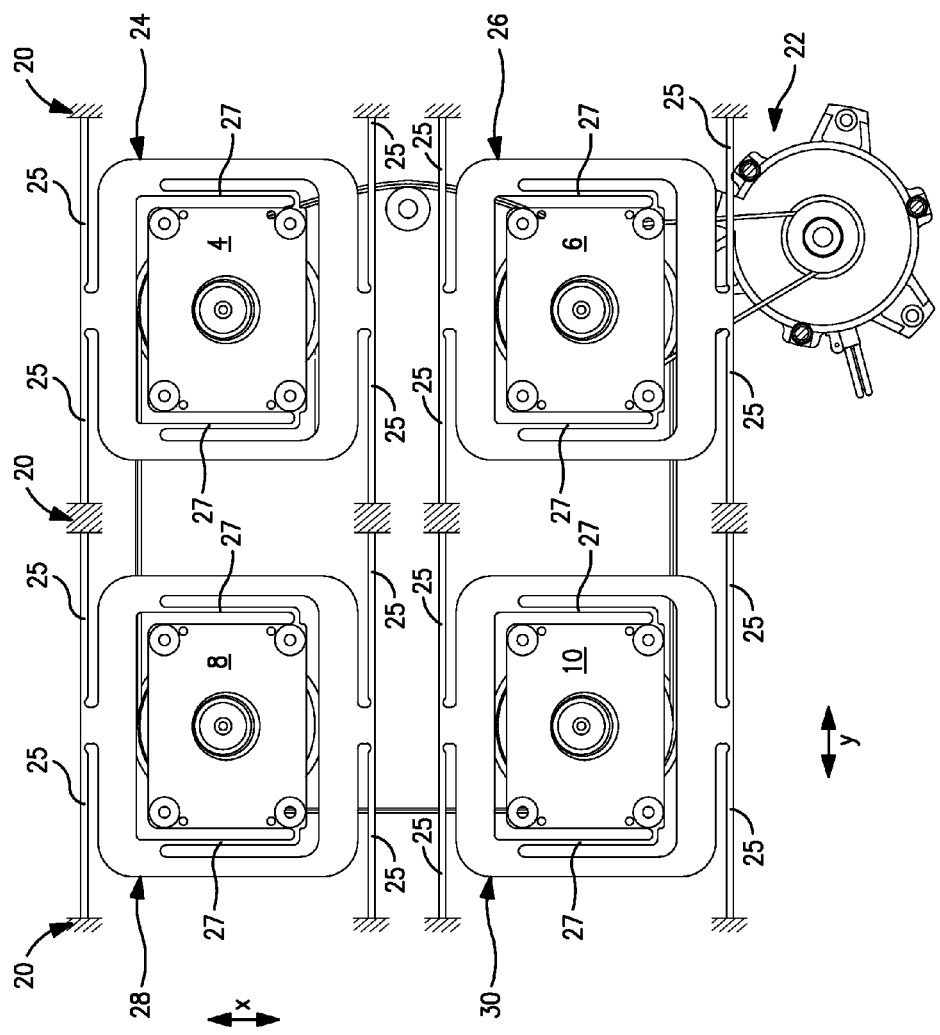
FIG. 3 shows a plan view of the drive mechanism and of the bearings of the four adapter plates of the device according to FIG. 1, without the inventive rotation in the direction of the mixing movement.

FIG. 3 shows a plan view of the inner structure of the drive mechanism 22 of the mixing device 2 according to FIG. 1 (without the inventive rotation of the starting position of the adapter plates in the direction of the mixing movement). The figure shows particularly clearly how the bearings 24, 26, 28 and 30 and the drive mechanism 22 permit the above-described mixing movement of the adapter plates 4, 6, 8 and 10 relative to the rest of the housing 20 (on which the drive motor for this mixing movement is also secured); each of the adapter plates 4, 6, 8 and 10 is mounted via the bearings 24, 26, 28 and 30 by means of a film-hinge arrangement 25 with a degree of freedom in direction x and a film-hinge arrangement 27 with a degree of freedom in direction y relative to the rest of the device. This allows the belt drive 22 to move the adapter plates 4, 6, 8 and 10 in the circular translatory oscillating mixing movement according to FIG. 4 in a horizontal plane (the drawing plane of FIGS. 2 to 5), while the film-hinge bearings do not permit any substantial movement out of the horizontal plane.

It will be seen from the schematic plan view according to FIG. 2 that the four adapter plates 4 to 10 rotate in the same direction (the small arrows at the centers of gravity S of the adapter plates indicate the respective rotation movement). It will also be seen that the midpoints $M_S$ of the rotation movement of the centers of gravity of the adapter plates 4 to 10 are arranged at the corner points of an imaginary rectangle 32. Since the spacing between the adapter plates 4 to 10 is of the order of magnitude of decimeters, while the radius of the rotation movement is of the order of magnitude of millimeters (in actual relationship to one another, not in the exaggerated schematic depiction in FIG. 3), this arrangement of the adapter plates 4 to 10 can according to the invention preferably be designated as "substantially mirror-symmetrical in plan view", namely with respect to the lines of symmetry 34, 36 extending at right angles to each other.

It will finally also be seen that the starting positions of the four adapter plates 4 to 10 are "rotated relative to one another": the adapter plates start their mixing movement (indicated by the small arrows at the centers of gravity S) from starting positions rotated in each case through 90° relative to one another, that is to say according to the preferred calculation according to the invention, dividing 360° by the total number of adapter plates. The centers of gravity S of the diametrically opposite adapter plates 4, 10 are rotated through 180° relative to each other, likewise the centers of gravity S of the two other diametrically opposite adapter plates 6, 8, and these adapter plate pairs 4, 10 and 6, 8 are in turn rotated through 90° relative to each other, always in relation to their respective rotational midpoints $M_S$.

In order to illustrate once again by way of example the "rotated relative to one another through 90°", reference is made to FIG. 5. The starting position of the adapter plate 8 is shown by dotted lines, while that of the adapter plate 4 is shown by solid lines. It will be seen that the (center of gravity of) adapter plate 4 is rotated through 90° relative to the (center of gravity of) adapter plate 8 (indicated about the rotational midpoint $M_S$ of the center of gravity).

The inventive effect of reducing undesired imbalance is therefore derived from the circular translatory oscillating mixing movement in a horizontal plane (thus, in the example shown, mechanically from the film-hinge bearing according to FIG. 3 with the resulting two translatory degrees of freedom of each adapter plate 4 to 10 (in the x direction and y direction of the horizontal movement planes) in which the adapter plates 4 to 10 are driven in rotation by the belt drive 22 (as is shown schematically according to FIG. 2)), together with the inventive rotation of the starting positions of the adapter plates through 90° relative to one another in the example shown.

The invention claimed is:

1. A multistation mixing device for mixing the contents of laboratory vessels, wherein the mixing device comprises:
   (a) at least two adapter plates, wherein each adapter plate has a holder for receiving laboratory vessels and, when seen in a plan view, the adapter plates are arranged mirror-symmetrically and/or uniformly on an imaginary circle, and
   (b) a drive mechanism capable of driving each of the adapter plates in a mixing movement with the same angular speed such that, in horizontal planes, each point of the adapter plate executes a circular movement with the same radius, the same angular speed and the same angular position about a respective midpoint,
   wherein the starting positions of the adapter plates, from which positions the adapter plates are driven by the drive mechanism, are rotated relative to one another by an angle in the direction of the mixing movement in their respective angular position, such that imbalances during the mixing movement are at least partially compensated.

2. The mixing device according to claim 1, wherein the drive mechanism drives the adapter plates in the same direction of rotation.

3. The mixing device according to claim 1, wherein the starting positions of the at least two adapter plates are rotated relative to each other by an angle that is calculated from 360° divided by the total number of adapter plates.

4. The mixing device according to claim 1, wherein:
   the total number of adapter plates is an even number of adapter plates;
   at least two of the adapter plates are diametrically opposed to each other; and
   the starting positions of diametrically arranged adapter plates are rotated relative to each other through 180°.

5. The mixing device according to claim 1, wherein groups of laboratory vessels are arranged in a holder.

\* \* \* \* \*